United States Patent [19]

Neti et al.

[11] 4,328,082

[45] May 4, 1982

[54] SOLID STATE ION-SENSITIVE ELECTRODE AND METHOD OF MAKING SAID ELECTRODE

[75] Inventors: Radhakrishna M. Neti, Brea; John N. Harman, III, Placentia, both of Calif.

[73] Assignee: Beckman Instruments, Inc., Fullerton, Calif.

[21] Appl. No.: 163,112

[22] Filed: Jun. 26, 1980

[51] Int. Cl.³ .......................................... G01N 27/36
[52] U.S. Cl. ............................................... 204/195 G
[58] Field of Search ............. 204/195 G, 195 M, 1 H; 128/635

[56] References Cited

U.S. PATENT DOCUMENTS

| | | | |
|---|---|---|---|
| 2,117,596 | 5/1938 | Bender et al. | 204/195 G |
| 3,649,506 | 3/1972 | Petersen et al. | 204/195 G |
| 3,787,307 | 1/1974 | Schwab et al. | 204/195 G |
| 4,105,509 | 8/1978 | Jungck | 204/1 T |
| 4,256,561 | 3/1981 | Schindler et al. | 204/195 M |
| 4,264,424 | 4/1981 | Niedrach | 204/195 S |

OTHER PUBLICATIONS

Toyoichi Tanaka, Scientific American, pp. 124-138, Jan. 1981.

*Primary Examiner*—G. L. Kaplan
*Attorney, Agent, or Firm*—R. J. Steinmeyer; P. R. Harder; Edward C. Jason

[57] ABSTRACT

A solid state ion-sensitive measuring electrode is disclosed in which a filler solution comprising sodium silicate is provided between an outer glass membrane of the electrode and an internal metallic wire which serves as a conductor from the electrode to a meter. The filler solution is inserted into the electrode as a liquid, and is subsequently dehydrated to provide a permanent solid-state matrix which is electrically conducting between the outer glass membrane and the internal wire.

11 Claims, 2 Drawing Figures

SOLID STATE ION-SENSITIVE ELECTRODE AND METHOD OF MAKING SAID ELECTRODE

BACKGROUND OF THE INVENTION

The present invention relates to ion-sensitive, or ion-selective, electrodes, and particularly to electrodes of the "membrane" type wherein a conductor extends into an electrode enclosure, or membrane, which has an ion-sensitive exterior immersed in the sample to be tested.

The primary intended use is as a pH sensor, wherein the exterior of the membrane is electrically sensitive to hydrogen ions. However, the invention also has utility with respect to electrodes which are sensitive to other types of ions, such as sodium ions or potassium ions. And sensors using the present invention may be used to measure such values as sulfate activity or halide activity.

The invention is primarily concerned with the problem of providing a suitable material for conducting the electrical signals generated at the membrane to the conductor which transmits the signals to an analyzer, which translates them into the desired data. In a pH sensor, the sensing of hydrogen ions at a measuring electrode, or half cell, is compared with data from a reference electrode, or half cell, to provide pH readings.

The conventional method of conducting electrical signals within the electrode has been the use of an aqueous buffered electrolyte filling the space between the membrane and the externally connected conductor. There are, however, certain obvious shortcomings resulting from the use of liquid electrolytes, such as the problems of "attitude-sensitivity" and of unfavorable response to significant temperature changes. The attitude-sensitivity problem requires complex sealing efforts to prevent leakage and, in addition to the leakage problem, also may cause a loss of electrical contact if the electrode is tipped. Furthermore, significant temperature increases can cause boiling of the liquid, with the attendant pressure buildup leading to destruction of the electrode.

One effort to solve the problem of attitudesensitivity has been the use of a gelled electrolyte in the electrode. In such a device, the membrane, or bulb, is totally filled with a gelled electrolytic material, which makes it attitude independent. However, in addition to the fact that gelled electrolytes may liquefy due to temperature increases, these gelled electrolytes suffer from their tendency to "poison" the pH response on the inner side of the pH responsive bulb, their susceptibility to degradation over a long period of time, and their possible instability in an ionizing environment, such as might be encountered in a field of radioactive flux.

Another prospective solution of the problems encountered by liquid-filled electrodes has been to provide a completely "solid-state" electrode. An exmple of this is shown in FIGS. 1 and 2 of Petersen et al. U.S. Pat. NO. 3,649,506, issued Mar. 14, 1972. In the device of the patent, the pH sensitive glass is melted and deposited as the outside layer on an electrode having a plurality of solid material layers. Devices of this type have experienced difficulties due to drift of their asymmetry (resting) potential. It is speculated that this drift may be caused by the different thermal coefficients of expansion of the pH sensitive glass and the solid material on which it is deposited. In other words, there may be a stability problem at the interface between the two materials. Another theory is that the pH sensitive glass, as it is deposited on the electrode, and as it changes from the molten state to the solid state, may tend to become devitrified and to lose the amorphous characteristic of glass, which would be detrimental to its functioning as a pH sensor.

The purpose of the present invention is to provide a more satisfactory solid-state ion-sensitive electrode, which will avoid the shortcomings of the devices discussed above.

SUMMARY OF THE INVENTION

The present invention is primarily the result of the discovery that the material sodium silicate can be successfully used as the "matrix", or "carrier", material in an electrolytic composition which provides the conductive "filler" in an ion-sensitive electrode. By inserting the sodium silicate as part of a liquid solution, and thereafter dehydrating the solution, a permanent solid state filler is provided which has the necessary electrical conducting capabilities.

More detailed aspects of the invention relate to the materials which are combined with the sodium silicate in the solution used as a filler and to the process by which the fabrication of the solid state electrode is accomplished.

DETAILED DESCRIPTION OF SPECIFIC EMBODIMENTS

Figure 1:
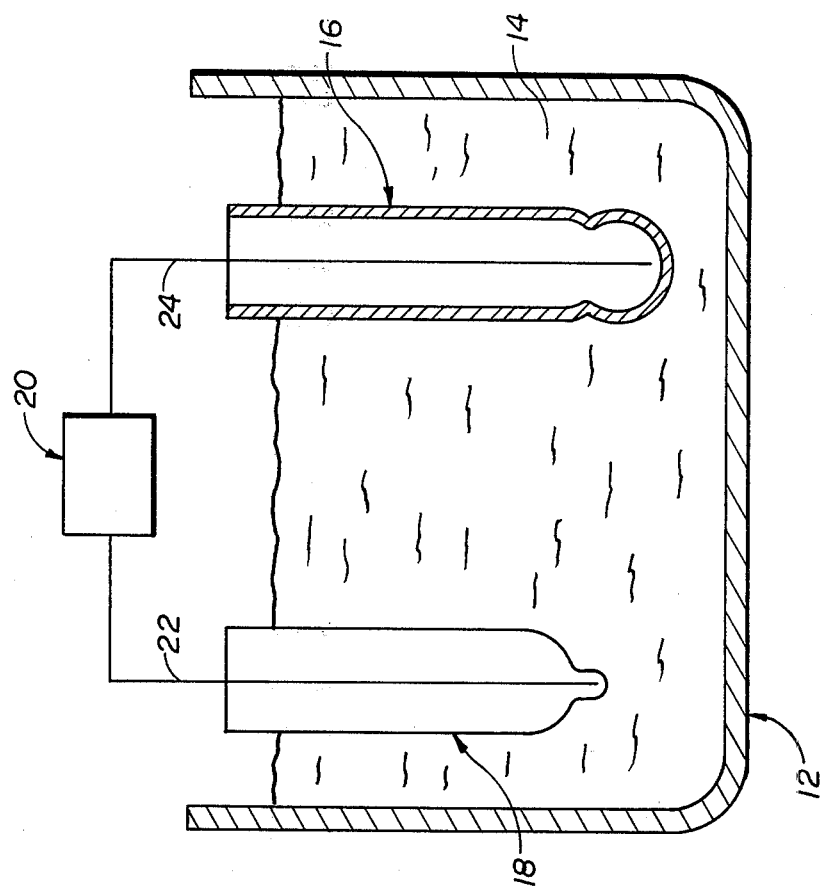
FIG. 1 is a sectional view showing a sample container in which a measuring electrode and a reference electrode are shown diagrammatically in a circuit including a pH indicator.

As a preliminary to a detailed discussion of the findings which are the heart of this invention, the structure shown in the drawings will be briefly described.

FIG. 1 shows, very simply, a type of system in which the present invention may be used. A container 12 has a quantity of liquid sample 14 therein, which is to be tested for a given characteristic, such as its pH value. A measuring electrode 16 and a reference electrode 18 are immersed in the liquid. A pH indicating device 20, which comprises a high impedance millivolt meter and suitable amplifying means, is connected by a wire conductor 22 to the reference electrode 18 and by a wire conductor 24 to the measuring electrode 16, thereby providing a complete circuit, including the sample liquid 14 between the electrodes.

The reference electrode 18 performs two necessary functions. One is the function of providing a second lead between the voltmeter and the sample 14. The other is the function of serving as a point of stable, constant comparison potential. Ideally, its potential is not ion-sensitive; and it maintains a constant potential regardless of the solution into which it is immersed.

As will be explained in greater detail below, the measuring electrode 16 is preferably buffered to provide zero potential difference between it and the reference electrode 18 when the sample has a pH of 7 and is at room temperature. The system is then so calibrated that the potential difference measured by the measuring electrode when both electrodes are placed in a sample having a different known pH value will indicate the correct value at the indicating device 20. The measuring electrode 16 is ion-sensitive, and develops a change in potential proportional to the concentration of hydrogen ions in the sample.

Figure 2:
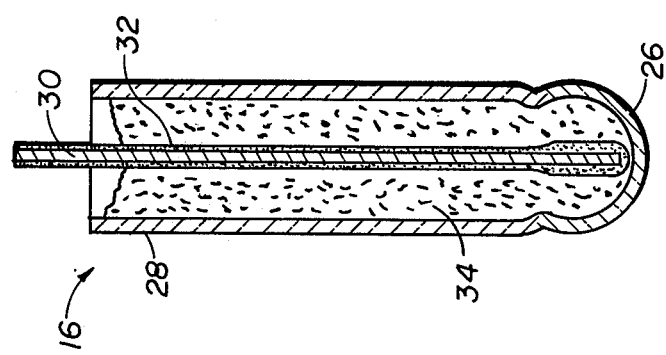
FIG. 2 is a sectional view taken through the measuring electrode of FIG. 1, which incorporates the concepts of the present invention.

FIG. 2 shows the elements of the measuring electrode, which constitute the significant improvements provided by the present invention. The housing, or enclosure, of the measuring electrode may be, typically, a glass element having the general shape of a tube provided with a spherically shaped lower end. The lower end 26 of the housing is formed of ion-sensitive glass and is fused onto the lower end of a tubular glass stem 28. This may be accomplished by the known practice of dipping the tubular stem 28 into a body of molten ion-sensitive glass and thereafter blowing the molten bead-like globule which adheres to the tubular stem 28 into the spherical, or bulb-shaped, membrane 26.

In the center of the electrode enclosure 26–28 is a suitable conducting material 30, which is in electrical contact with indicating device 20 via wire 24. Preferably, conductor 30 is a metallic wire. In one effective version of the invention, the wire is a silver wire having a silver halide coating; and in another effective version, the wire is an uncoated copper wire.

If silver is the material used, the silver wire 30, together with its coating 32, constitutes a half cell, which cooperates with the half cell provided by the reference electrode, thereby providing a complete electrical circuit in conjunction with the electrolytic sample fluid. The coating 32 on wire 30 then is a part of the electrode structure because the half cell requires the combination of the metallic conductor and a metallic-halide coating. Coating 32 should be a silver halide if silver is the metal of conductor 30. Either silver bromide (AgBr), silver chloride (AgCl), or silver iodide (AgI) may be used. However, for reasons discussed below, it appears that silver bromide is the preferred coating material. The coating is applied to the wire by dipping the silver wire into molten silver bromide, which will adhere to the wire when it is removed and solidify as a coating. If copper is used as the material of wire 30, it does not require a coating.

The space between the conductor 30 and the glass enclosure 26–28 is filled with a material 34, which is either sodium silicate alone, or a homogeneous mixture of sodium silicate with one or more other chemical compounds. The filler material 34 is inserted into the enclosure 26–28 as a liquid solution. It is then dehydrated to form a permanent solid-state solution, which provides an electrically conducting "bridge" between the ion-sensitive membrane 26 and the wire 30.

The constituency of the filler material 34, and the method of handling it, constitute the heart of the present invention. And the material which has solved the problem of providing a matrix, or carrier, for the filler material is the primary discovery required to make a solid-state electrode practicable. The material, as already stated, is sodium silicate, which was originally not considered as a possible solution of the problem, but which was tried after many other materials, considered more promising, had failed.

There were two problems of particular seriousness, which were encountered with other materials tried as fillers for the electrode. One was the problem of the filler peeling away from the surface either of the glass membrane or of the metal wire. In other words, to be satisfactory, the filler must permanently adhere to both the membrane and the wire, in order to provide continuous electrical conduction. The other major problem was cracking of the ion-sensitive glass membrane 26 during temperature cycling testing of the material. This testing involved either continuous, or intermittent, testing of the pH instrument as the temperature of the electrode (either dry or immersed in a buffer material) was raised from the ambient temperature to a high in the neighborhood of 85° C. to 95° C., and then cooled back to the ambient temperature. During such temperature cycling the pH readings were observed to assess the performance of the electrode.

Among the filler materials which were first tried, those which did not tend to lose electrical continuity because of lack of adhesion, invariably caused cracking of the membrane 26, or of its connection to the tube 28, as the temperature cycling was performed. While the reason for the cracking problem is not known to applicants, it can be theorized that the problem resulted from the substantial difference between the thermal coefficients of expansion of the filler material and the glass membrane.

The first materials tried unsuccessfully were carbon in an aqueous solution, and colloidal carbon in an aqueous dispersion (Aquadag), both of which were dehydrated to form a solid-state filler. The primary problem encountered with the carbon material was peeling away from the glass membrane; and the primary problem encountered with the Aquadag was dislodging of the metal wire, thereby losing electrical continuity. Subsequently, several materials were tried which were injected into the electrode in the solid-state form, including dental amalgam, powdered potassium chloride (KCl), a powdered combination of silver chloride (AgCl) and potassium chloride (KCl), and molten silver chloride (AgCl). The powdered potassium chloride failed because contact with the wire was intermittent; and the other three identified materials failed because of cracking of the glass membrane during temperature cycling. Other filler materials tried were silver-filled epoxy, a paste material, which caused cracking of the glass membrane; and gelled potassium chloride (KCl), a highly viscous material, which caused "poisoning" of the glass membrane, i.e., it caused the membrane to lose its ion-sensitivity.

The possibility of using sodium silicate as the basic ingredient of a solid-state measuring electrode was conceived after thousands of individual tests on materials of the types discussed above. The decision to try sodium silicate as the primary ingredient of the filler material led to elimination of the cracking and peeling problems. Furthermore, use of sodium silicate provided a sufficiently broad pH span to constitute a satisfactory electrode. The primary difficulty presented by the initial experiments using sodium silicate was its asymmetry potential, which placed the electrode quite far into the acidic portion of the pH spectrum. Subsequent experiments were directed primarily toward combining the sodium silicate with materials which would bring the asymmetry potential of the filler close to pH 7. In an extensive series of tests, various electrodes using sodium silicate as the primary filler material were tested in buffer solutions having known values of pH 4, pH 7, and pH 10, respectively, thereby providing data both as to the asymmetry potential of the electrodes being tested and as to their pH span.

The following are a few of the specific examples tested, out of a total of at least 300, which demonstrated the progress made once sodium silicate had been identified as a desirable filler matrix.

The first experiment using sodium silicate combined a 40% sodium silicate solution in the measuring electrode with an Ag/AgCl internal half cell. After dehydration of the sodium silicate solution, the electrode was tested. That electrode exhibited a satisfactory pH span when tested in the pH 4–10 range, but the asymmetry potential moved to an extremely acid value.

In a subsequent experiment, a special electrode filler mixture was made having one part of Beckman Instruments #73175 internal electrode filling solution combined with three parts of sodium silicate solution. The electrode was dried in an oven overnight at 65° C. It was then tested, with the following results:

| Buffer pH | Electrode pH Readings |
|---|---|
| 4.0 | −1.9 |
| 7.0 | 1.0 |
| 10.0 | 4.0 |

As can be readily seen from the test results, the pH span of that electrode was adequate, but the asymmetry potential was very acidic in comparison with commercially available liquid-filled glass electrodes. However, the test was considered very promising because, after drying in the oven, the electrode bulb did not develop any cracks, which constituted a significant improvement over materials previously tested.

In a subsequent experiment, 20 cc of sodium silicate solution was mixed with 10 cc of saturated potassium chloride solution. The glass electrode was filled with this solution and tested for asymmetry potential and span in the pH 4 to 10 range. The asymmetry potential moved up to pH 3.0 in a 7.0 pH buffer.

In a later series of experiments, the internal solution was made by mixing sodium silicate solution with powdered potassium chloride. This was tested for asymmetry potential with the following results:

| Composition of the Internal Filling | Asymmetry Potential (in pH Units) |
|---|---|
| 80% sodium silicate +20% KCL powder | 4.5–4.7 in 7.0 pH buffer |
| 50% sodium silicate +50% KCL powder | 5.75 in 7.0 pH buffer |
| 1 cc of sodium silicate +3.2 gm of KCL powder | 1.2 in 4.0 pH buffer |
| 1 cc of sodium silicate +10 gm of KCL powder | 2.5 in 4.0 pH buffer |

These experiments showed that the asymmetry potential could be changed by controlling the combination of the sodium silicate and an alkali halide, such as potassium chloride.

In another experiment the pH glass bulb was filled with sodium silicate and a copper wire was used in place of the Ag/AgCl half cell. This gave a surprisingly good performance.

| Buffer pH | Observed pH Readings |
|---|---|
| 4.0 | 4.0 |
| 7.0 | 6.85 |
| 10.0 | 9.75 |

While the asymmetry and span data of the sodium silicate and copper wire combination are very favorable, this combination was not chosen for further development because the available reference electrodes are not sufficiently compatible with copper in the measuring electrode, particularly when the potentials are affected by temperature changes. In other words, use of the copper-sodium silicate combination would require a major redesign of the system, and would not appear to provide a solid-state measuring electrode compatible with existing reference electrodes.

Another test was made with a sodium silicate solution combined with a platinum screen and wire. This combination provided the following results:

| Buffer pH | Observed pH Readings |
|---|---|
| 4.0 | 2.0 |
| 7.0 | 4.9 |
| 10.0 | 8.0 |

The most desirable results, indicating the best mode presently known, were experienced in a series of tests (approximately 200) using a filling solution comprising substantially equal quantities by volume of (a) a commercially available 40% aqueous solution of sodium silicate, and (b) a saturated solution of potassium bromide. To this composition was added trace quantities (up to 1%) of silver bromide. This solution was used in conjunction with a silver/silver bromide half cell as the externally connected conductor. The solution in the electrode was dehydrated and then tested. Three series of tests were conducted. The first series used material which had been dried in the oven at 80° C. for six hours. The second series of tests used material which had received further drying for six additional hours at 80° C. And the third series of tests used material which had been further dried overnight at 80° C. The tests for span an asymmetry showed these results:

| Buffer pH | Observed pH Readings | | |
|---|---|---|---|
| | 1st Series | 2nd Series | 3rd Series |
| 4.0 | 3.4 | 3.6 | 4.2 |
| 7.0 | 6.4 | 6.65 | 7.15 |
| 10.0 | 9.1 | 9.6 | — |

The test results just cited indicated that a satisfactory solution of the problems had been arrived at. Furthermore, the same electrode which provided those test results was again tested after a long time interval, with very satisfactory conclusions. The previously stored electrode was tested using a calomel reference electrode, and the tests were compared with a commercially available glass electrode having a liquid filler. The comparative data were as follows:

| Buffer pH | Commercial Liquid-Filled Electrode/ Calomel Reference | Sodium Silicate Combination/Calomel Reference |
|---|---|---|
| 4.0 | 3.35 | 3.4 |
| 7.0 | 7.0 (set) | 7.05 |

| Buffer pH | Commercial Liquid-Filled Electrode/ Calomel Reference | Sodium Silicate Combination/Calomel Reference |
|---|---|---|
| 10.0 | 8.95 | 8.9 |

The sodium silicate solution appears to provide an answer to the problem of developing an effective solid-state electrode because of the following properties, which were demonstrated by numerous experiments:

(a) The sodium silicate material can be readily converted from a homogeneous liquid solution to a stable and homogeneous solid solution. The dehydration process is easy to accomplish and not damaging to the electrode.

(b) The sodium silicate material adheres permanently to both the glass membrane and the wire.

(c) The sodium silicate acts as an electrical conductor between the glass membrane and the wire.

(d) Apparently because of its glass-like characteristics, the sodium silicate filler does not cause cracking of the glass membrane, as many other fillers do.

(e) The liquid sodium silicate solution is readily miscible with other materials, such as alkali halides, which are useful in adjusting the asymmetry potential.

The sodium silicate solution could be used alone as the filler material in the electrode. However, the strongly acidic asymmetry potential would make it difficult to use such an electrode with an existing pH measurement system. It would be necessary to calibrate the system radically to compensate for the asymmetry potential problem.

It is clearly preferable to provide an asymmetry adjustment, or tuning, by mixing the sodium silicate solution with suitable pH compensating material. The purpose is to insure a set potential of the silver/silver halide half cell, and to insure electrochemical revesibility of the half cell. The materials which appear to be most satisfactory in compensating for the asymmetry potential deviation of the sodium silicate are alkali halides. And while a plurality of alkali materials can be used in such compounds, including sodium and potassium, and a plurality of halides can be used in such compounds, including chloride, bromide or iodide, potassium bromide has provided the best asymmetry adjustment of any material thus far tried.

It appears also that the use of a small amount of silver bromide in the sodium silicate solution is useful in "tuning" the asymmetry of the electrode. Maintenance of stable potential values is promoted by using bromide as the halide in both the alkali halide and the metal halide material.

The metal halide used as the coating 32 on the wire preferably is the same as the metal halide included in the solution. One reason for using the metal halide in the solution is to prevent depletion of the coating material on the wire. The amount of silver halide in the filler solution is limited to less than 1% by the fact that larger amounts will not remain in solution. Generally, it is desirable to include in the solution as much metal halide as will dissolve.

The alkali halide, which, as stated, is preferably potassium bromide, acts as an electrical conducting material in the solid solution, which is very desirable. The amount of such material used is determined by the asymmetry adjustment requirement. If handled as a saturated solution, or as a powdered material, when combined with the sodium silicate solution, the alkali halide minimizes the subsequent drying requirements. However, fine "tuning" of the asymmetry potential may be accomplished by combining unsaturated solutions of alkali halide with the sodium silicate solution.

Various forms of sodium silicate may be used. The one used in the experiments discussed herein had the formula $Na_2Si_3O_7 \times H_2O$. The same principles of operation would also apply to other forms of sodium silicate, such as $Na_6Si_2O_7$ and $Na_2SiO_3$ (sodium metasilicate). The lower limits of the amount of sodium silicate, and of the percentage of sodium silicate in the aqueous solution, are controlled by the requirement that a suitable supporting matrix must be provided to maintain electrical contact, after dehydration, between the membrane and the metallic conductor or half cell. In other words the sodium silicate and/or the mixture containing sodium silicate must maintain continuity in the solid-state condition. The upper limits of the amount of sodium silicate, and of the percentage of sodium silicate in the aqueous solution, are controlled by the need to maintain a homogeneous solution. If the concentration of sodium silicate is too high, as in a saturated solution of sodium silicate, the homogeneity of the solution may be lost.

The following claims are intended not only to cover the specific embodiments disclosed, but also to cover the inventive concepts explained herein with the maximum breadth and comprehensiveness permitted by the prior art.

What is claimed is:

1. A method of fabricating an ion sensitive solid-state electrode which includes the steps of:
   forming a hollow ion-sensitive glass member;
   inserting an electrically conducting member into the interior of the glass member;
   filling the interior of the glass member around the conducting member with an electrically conducting aqueous solution of an alkali halide and a sodium silicate compound; and
   dehydrating the aqueous solution at an elevated temperature, thereby converting said solution into a solid anhydrous body which provides a continuous electrically conductive bridge between the glass member and the conducting member.

2. The method of claim 1 in which the elevated temperature is greater than approximately 80° C.

3. The method of claim 1 or 2 in which the elevated temperature is maintained for a time greater than approximately six hours.

4. The method of claim 1 in which said conductive member comprises a metal conductor coated with a halide of that metal, and in which said solution includes a quantity of said metal halide.

5. An ion-sensitive electrode comprising:
   a hollow glass member having an end portion which is ion-sensitive and which is adapted to be immersed in a sample to be tested;
   a conductive member which extends into the interior of the glass member and which is adapted to be connected to an electrical indicating device;
   a solid, anhydrous electrically conductive body that is permanently adherent to the interior of the glass member and to the conductive member, said body being produced by:
   (a) introducing into the glass member an aqueous solution of an alkali halide and a sodium silicate compound, and (b) maintaining the solution-containing glass member at an elevated temperature to dehydrate said solution and convert the same to said solid, anhydrous body.

6. A ion-sensitive electrode as set forth in claim 5 in which the quantity of the alkali halide is sufficient to bring the asymmetry potential of the electrode to a value corresponding to an approximately neutral pH.

7. An ion-sensitive electrode as set forth in claim 5 in which the conductive member comprises a metal conductor having a coating of the halide of that metal.

8. An ion-sensitive electrode as set forth in claim 7 in which the metal is silver and in which the metal halide is selected from the group consisting of silver chloride, silver bromide and silver iodide.

9. An ion-selective electrode as set forth in claim 5 in which the conductive member includes a metal conductor coated with a halide of that metal, and in which said body includes a quantity of said metal halide.

10. The ion-senstive electrode of claim 5 in which said elevated temperature is greater than approximately 80° C.

11. The ion-sensitive electrode of claim 5 or 10 in which the elevated temperature is maintained for a time greater than approximately six hours.

* * * * *